(12) United States Patent
Zhao et al.

(10) Patent No.: US 6,908,632 B1
(45) Date of Patent: Jun. 21, 2005

(54) BLOOD GLUCOSE MODULATING COMPOSITIONS AND METHODS

(75) Inventors: Chunsheng Zhao, Beijing (CN); Jingyan Wang, Beijing (CN); Yan Zhang, Beijing (CN); Weiti Yin, Beijing (CN); Decheng Zhang, Shanghai (CN); Jia-Shi Zhu, San Diego, CA (US)

(73) Assignee: Pharmanex, LLC

( * ) Notice: Subject to any disclaimer, the term of this patent is extended or adjusted under 35 U.S.C. 154(b) by 0 days.

(21) Appl. No.: 10/420,347

(22) Filed: Apr. 21, 2003

Related U.S. Application Data

(60) Provisional application No. 60/374,196, filed on Apr. 19, 2002.

(51) Int. Cl.$^7$ ................................................ A61K 35/78
(52) U.S. Cl. ........................ 424/765; 424/774; 424/725
(58) Field of Search ................................ 424/776, 765, 424/725; 514/866

(56) References Cited

U.S. PATENT DOCUMENTS

| | | | |
|---|---|---|---|
| 6,358,999 B2 | 3/2002 | Fujimura et al. | |
| 6,361,807 B1 | 3/2002 | Aviram et al. | |
| 6,365,628 B1 | 4/2002 | Berge | |
| 6,368,597 B1 | 4/2002 | Strassmann et al. | |
| 6,369,072 B2 | 4/2002 | Malamas et al. | |
| 6,485,760 B2 * | 11/2002 | Matsuyama | 424/775 |

FOREIGN PATENT DOCUMENTS

| | | | |
|---|---|---|---|
| CN | 1141788 A | * | 2/1997 |
| EP | 1022022 A1 | | 7/2000 |
| JP | 56073027 A | * | 6/1981 |
| JP | 62067028 A | * | 3/1987 |
| JP | 08217682 A | * | 8/1996 |
| JP | 08217688 A | * | 8/1996 |

OTHER PUBLICATIONS

Roman–Ramos et al. Arch. Invest. Med. 1991. vol. 22, pp. 87–93, full journal article enclosed.*

Polly Hitchcock Noel et al., The use of Traditional Plant Medicines for Non–Insulin Dependant Diabetes Mellitus in South Texas, Phytotherapy Research 1997 11:512–517.

Roman–Ramos, R et al., Experimental Study of the Hypoglycemic effect on some antidiabetic plants. Arch Invest Med. (Mex.) 1991 22(1) :87–93.

W. Noreen et al., Effect of *Eriobotrya japonica* on Blood Glucose Levels of Normal and Alloxan–Diabetic Rabbits, Planta Medica 1998, 54(3):196–9.

Naoko Nozato et al., Triterpenes from the leaves of *Eriotrya japonica*, Natural Medicine 1994 48(4): 336.

Nunziatina De Tommasi et al., Hypoglycemic Effect so Sesquiterpene Glycosides and Polyhydroxylated Triterpenoids of *Eriobotrya japonica*, Planta Med 1991,57:414.

* cited by examiner

*Primary Examiner*—Christopher R. Tate
(74) *Attorney, Agent, or Firm*—Thorpe North & Western, LLP

(57) ABSTRACT

Loquat extracts and methods for the preparation and use thereof in modulating blood glucose metabolism are disclosed and described. In one aspect, the present invention includes a Loquat extract having a standardized corosolic acid content, and a method for the production thereof.

5 Claims, 5 Drawing Sheets

BLOOD GLUCOSE MODULATING COMPOSITIONS AND METHODS

PRIORITY DATA

This application claims priority to United States Provisional Patent Application Ser. No. 60/374,196, filed on Apr. 19, 2002, which is incorporated herein by reference.

FIELD OF THE INVENTION

The present invention relates generally to compositions and methods for modulating blood glucose levels. Accordingly, the present invention involves the fields of health science, nutrition, and medicinal chemistry.

BACKGROUND OF THE INVENTION

Glucose metabolism disorders, such as diabetes mellitus, insulin resistance, hyperglycemia, and hyperinsulinemia, are some of the most common endocrine diseases experienced today. A number of factors have traditionally thought to be responsible for such conditions, including genetics, viral illness, and obesity. Recently, obesity has been named as a leading risk factor in the development of such conditions. Obesity is quickly reaching epidemic proportions in many parts of the world. This increase is largely blamed on changes dictated by modern lifestyles that have reduced daily physical activity, and on the abundance and availability of food.

Other aspects of many modern lifestyles and food technology seem to have further increased the incidence of obesity and glucose metabolism disorders. Particularly, the lifestyles of many people require that they frequently eat meals at restaurants, rather than meals prepared at home. Further, as a matter of convenience, many of the meals prepared at home today include, or may consist entirely of, pre-prepared portions that were obtained frozen, dehydrated, canned, or otherwise preserved, for quick and easy reconstitution. These pre-prepared foods, the foods obtained while dining at a restaurant, and other foods, such as soda pop, pastries, cookies, and candy, have become increasingly available, and most often contain high amounts of sugar, fat, salt, and other chemical preservatives. It is now thought that the consumption of such foods in significant quantities further increases the onset of various glucose metabolism disorders in and of itself, and further, is a contributory factor along with obesity. Sustained consumption of large amounts of sugar or other simple carbohydrates has particularly been identified as reducing insulin sensitivity.

The most frequent treatment for many glucose metabolism disorders is the administration of insulin. It is well known that insulin is the key substance produced in the body for facilitating glucose metabolism. In fact, most glucose metabolism disorders are a result of the body's inability to produce a sufficient amount of insulin to meet the demands presented by glucose concentration in the blood. While insulin administration is a life-saving procedure for many individuals, once insulin supplementation is commenced, it can almost never be stopped. Thus, many individuals become dependent on insulin supplementation for life. Additionally, the only currently approved method for insulin administration is via injection, which is painful and inconvenient.

Alternative methods for addressing various glucose metabolism disorders, rather than insulin supplementation, have also been sought. Such methods include both prophylactic and responsive measures. Specific examples of various proposed solutions include administration of certain proteins, peptides, nucleotides, and other bioactive agents. Such are found, for example, in U.S. Pat. Nos. 6,358,999, 6,361,807, 6,365,628, 6,368,597, 6,369,072, and European Patent Application No. 1,022,022, each of which is incorporated herein by reference. While a number of these specific measures may provide effective prevention or relief of various glucose metabolism disorders, many are expensive and time consuming, and may present various undesirable side effects.

Therefore, compositions and methods for treating and preventing blood glucose metabolism disorders continue to be sought through ongoing research and development efforts.

SUMMARY OF THE INVENTION

Accordingly, the present invention encompasses compositions and methods for modulating blood glucose levels. In one aspect, the present invention provides a method for preparing a Loquat extract, and a method of modulating blood glucose levels using such an extract. The method of preparing the Loquat extract may include the steps of: 1) providing a Loquat source material, 2) partitioning the Loquat source material into small pieces, 3) soaking the pieces in an aqueous solution of water and from about 1% to about 95% ethanol at a temperature of from about 40° C. to about 95° C. for about 1 to about 4 hours, to create an extract solution, 4) filtering the extract solution and collecting the filtrate, and 5) concentrating the filtrate. Notably, at the end of the filtering portion of the process, the small pieces of Loquat may be collected and subjected to repeated soakings (i.e. 1 to 4 additional soakings) order to obtain additional extract from the pieces. The concentrated filtrate may then be dried, such as by freeze-drying, and then pulverized to provide a powdered extract. Further, when multiple soakings are performed, the filtrate collected from each may be combined prior to the step of concentrating.

The Loquat extract resulting from the extraction process described herein, may be incorporated into a variety of formulations for administration to a subject, or may be administered by itself. In one aspect, the Loquat extract produced by the process may yield a standardized corosolic acid content of about 7% w/w of the extract. Other standardized corosolic acid contents may be obtained by varying certain aspects of the extraction process. In view of such standardization, blood glucose modulating compositions may be made to include a therapeutically effective amount of Loquat extract and contain a specifically desired amount of corosolic acid. In one aspect, the amount of extract administered in order to achieve therapeutically effective results may be from about 0.5 mg to about 25 mg. Specific dosage regimens sufficient to achieve and maintain long-term blood glucose modulation or metabolism increasing results, may be determined by those of ordinary skill in the art.

In addition to the above-recited extraction methods and resultant compositions, the present invention includes a method of moderating blood glucose levels by administering the extract, or a composition containing the extract, to a subject.

The above-recited features of the invention will become apparent from a consideration of the following detailed description.

DETAILED DESCRIPTION OF THE INVENTION

Figure 1:
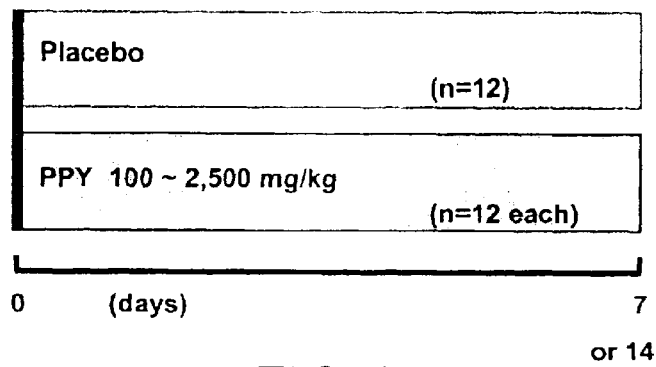
FIG. 1 shows a graphical representation of the subjects having normal glucose levels enrolled in a clinical study using compositions employing a Loquat (Pi Pa Ye "PPY") extract obtained using an extraction process in accordance with one embodiment of the present invention.

Before the present blood glucose modulating compositions and accompanying methods are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and, "the" include plural referents unless the context clearly dictates otherwise. Thus, for example, reference to an "excipient" includes reference to one or more of such excipients.

Definitions

In describing and claiming the present invention, the following terminology will be used in accordance with the definitions set forth below.

The terms "formulation" and "composition" may be used interchangeably herein. The terms "drug," "active agent," "bioactive agent," "pharmaceutically active agent," "neutraceutical active agent," "pharmaceutical," and "neutraceutical," are also used interchangeably to refer to an agent or substance that has measurable specified or selected physiologic activity when administered to a subject in an effective amount. These terms of art are well-known in the pharmaceutical, neutraceutical, and medicinal arts.

The term "extract" when used in connection with a plant, refers to one or more active agents, or a composition containing such, that is obtained from the plant, or a portion thereof, including the flower, fruit, seed, peel, leaf, root, and bark. As will be recognized by those of ordinary skill in the art, extracts may be either crude or refined to a selected degree in order to isolate specified active agents. A number of extraction processes that can be employed to produce the compositions of various types will be recognized by those of ordinary skill in the art.

As used herein, "Loquat" refers to the plant species Eriobotrya japonica, (Thunb.) Lindl. of the family rosaceae, also known by various common names such as Rosaceae Advance, Champagne, Early Red, Japanese medlar, Pi Pa Ye, Japanese plum, Nispero, etc., including all well known strains, variations, and hybrids thereof, grown anywhere in the world.

As used herein, in connection with pieces of Loquat source material, "small" refers to a piece having a size that allows reasonable extraction of active agents from the piece. Those of ordinary skill in the art will recognize a variety of specific piece sizes that will allow the active agents to be removed into a liquid, or other medium.

The terms "effective amount," and "sufficient amount" may be used interchangeably and refer to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating a condition for which the active agent is known to be effective. Various biological factors may affect the ability of a substance to perform its intended task. Therefore, an "effective amount" or a "therapeutically effective amount" may be dependent on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical, nutraceuticai, herbaceutical, and health sciences. See, for example, Meiner and Tonascia, "Clinical Trials: Design, Conduct, and Analysis," *Monographs in Epidemiology and Biostatistics*, Vol. 8 (1986), incorporated herein by reference.

As used herein, "carrier" or "inert carrier" refers to a polymeric carrier, or other carrier vehicle with which a bioactive agent, such as a cortisol moderator, and other anti-stress agents may be combined to achieve a specific dosage formulation. As a generally principle, carriers must not react with the bioactive agent in a manner which substantially degrades or otherwise adversely affects the bioactive agent.

As used herein, "subject" refers to a mammal that may benefit from the administration of a stress moderating composition or method as recited herein. Most often, the subject will be a human.

As used herein, "administration," and "administering" refer to the manner in which a bioactive agent, such as corosolic acid, or various sesqiterpenoids, is presented to a subject. Administration can be accomplished by various art-known routes such as oral, parenteral, transdermal, inhalation, implantation, etc. Thus, an oral administration can be achieved by swallowing, chewing, or sucking of an oral dosage form comprising the bioactive agent. Parenteral administration can be achieved by injecting a bioactive composition intravenously, intra-arterially, intramuscularly, intrathecally, or subcutaneously, etc. Transdermal administration can be accomplished by applying, pasting, rolling, attaching, pouring, pressing, rubbing, etc., of a transdermal preparation onto a skin surface. These and additional methods of administration are well-known in the art.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or subranges encompassed within that range as if each numerical value and sub-range is explicitly recited.

As an illustration, a numerical range of "about 1% w/w to about 5% w/w" should be interpreted to include not only the explicitly recited values of about 1% w/w to about 5% w/w, but also include individual values and sub-ranges within the indicated range. Thus, included in this numerical range are individual values such as 2, 3, and 4 and sub-ranges such as from 1–3, from 2–4, and from 3–5, etc. This same principle applies to ranges reciting only one numerical value. Furthermore, such an interpretation should apply regardless of the breadth of the range or the characteristics being described.

The Invention

Applicant has discovered an extraction process that provides a Loquat extract that is standardized to contain specific amount of certain ingredients, such as corosolic acid, which have been found to have a significant modulating effect on blood glucose levels when administered to a subject. This modulating effect is due at least in part to an increase in glucose metabolism by the cells as catalyzed by the Loquat extract. As such, the present invention extends not only the process of making a Loquat extract, but also to compositions incorporating such an extract, and methods of using the extract, or compositions containing the extract.

The extraction process of the present invention includes the following general steps. After Loquat source material has been obtained, it is partitioned into smaller pieces. The small pieces are then soaked in an aqueous solution for about 1 to about 4 hours to form an extract solution. The extract solution is filtered, and the filtrate containing the target active agents is collected and concentrated. Following concentration, the filtrate may be dried, such as by freeze-drying, in order to provide an extract having a solid form.

The partitioning of Loquat source material in the process of the present invention may be achieved by a variety of actions suitable for creating small pieces, such as chopping, cutting, tearing, grinding, smashing, etc. Those of ordinary skill in the art will readily recognize a variety of specific tools suitable to accomplish the desired partitioning activity. Further, the size into which Loquat pieces are partitioned may also be varied, and may impact the specific parameters required of other steps in the method of the present invention, such as the step of soaking. For example, material which is partitioned into smaller pieces may require a shorter soaking time, and/or a lower soaking temperature in order to achieve the same extract solution, than material that is partitioned into larger pieces. Those of ordinary skill in the art will recognize this principle, and be able to optimize piece size and soak time in order to maximize or custom tailor the extraction process in order to obtain a specific result.

Various soaking conditions may be used in the course of the present extraction method, in order to achieve a specific final Loquat extract. Specific conditions, such as the content and temperature of the aqueous solution, as well as the time of soaking may be varied. In one aspect of the present invention, the aqueous solution may include distilled water, and from about 1% to about 95% ethanol. In another aspect, the ethanol concentration may be greater than about 50%. In yet another aspect, the ethanol concentration may be greater than about 80%. In an additional aspect, the ethanol concentration may be greater than about 90%. In one aspect of the invention, the temperature of the aqueous solution may be from about 40° C. to about 95° C. In another aspect, the temperature may be from about 50° C. to about 80° C. In yet another aspect, the temperature may be about 70° C. In a further aspect, the temperature may be about 90° C. As noted above, the amount of time for which the Loquat pieces are soaked may be from about 1 to about 4 hours. However, in one aspect, the amount of time may be about 2 hours. In another aspect, the time may be about 1 hour.

After the Loquat pieces have been sufficiently soaked, the resultant extract solution is filtered to separate the pieces from the liquid filtrate containing the desirable bioactive agents. Such filtering may be accomplished using a number of specific filtration processes known to those of ordinary skill in the art, such as reduced pressure vacuum filtration, and may employ a number of different suitable filter types, such as paper filters, etc. At this point it should be noted that once the liquid is separated from the Loquat pieces, that the pieces may be reclaimed and soaked again in order to further extract remaining target bioactive agents therefrom. Subsequent soakings may utilize either the same conditions or different conditions as in the original or first soaking, as required in order to continue to draw the desired agents out of the leaf pieces, and into the aqueous solution. Following such additional or subsequent soakings, the respective extract solutions are filtered and the Loquat pieces are removed and discarded.

The filtrate (i.e. liquid containing the desired bioactive agents), or extract solution is now collected, and combined with other extract solutions, if multiple soakings are performed. The ethanol is then removed therefrom by any suitable method known to those of ordinary skill in the art, such as distillation, filtration, separation reaction, etc. The remaining extract is then condensed or concentrated. In some aspects, the concentrated extract may further be dried, such as by freeze-drying, or other techniques known to those of ordinary skill in the art, in order to provide a solid or powdered form extract. Such an extract may then be combined with other ingredients to provide a suitable dosage form for administration as discussed in further detail below.

A variety of Loquat parts may be utilized as the source material upon which the extraction is performed such as fruit, roots, stems, or combinations thereof, However, in one aspect, the source material may include Loquat leaves. In another aspect, the source material may consist of Loquat leaves.

In one aspect of the present invention the extraction process may yield an extract that is standardized to contain 7% w/w of the active ingredient corosolic acid. This standardized content allows various dosage formulations to be made which contain a target corosolic acid dosage. While a variety of amounts may be used, in one aspect, the composition may be formulated to contain from about 0.5% w/w to about 20% w/w corosolic acid. Other bioactive agents that are thought to also play a role in facilitating glucose metabolism, such as various sesqiterpenoids, are also contained in the Loquat extract obtained by the extraction process of the present invention.

The compositions containing the Loquat extract of the present invention may be formulated for administration through various known routes of administration, such as oral, parenteral, and transdermal routes. Examples of oral dosage formulations include without limitation, tablets, capsules, liquids, suspensions, powders, effervescent beverages, lozenges, soft gels, chewing gum, candy, etc. Examples of transdermal routes of administration include without limitation, topical formulations, such as lotions, cremes, gels, and pastes, and transdermal patches, such as liquid reservoir patches, plasters, and adhesive matrix patches. Suitable ingredients required to produce a particular formulation, such as specific carriers, excipients, binders, penetration enhancers, etc., will be readily recognized by those of ordinary skill in the art.

By way of example, without limitation when preparing an oral dosage formulation, such as a tablet, capsule, or powder, the active ingredients may be mixed with a lubricant such as a polyethylene glycol 6000, and a binding agent such as polyvinyl pyrrolidone. A wide range of known lubricants such as sodium benzoate, sodium lauryl sulfate, and other polyethylene glycols having an average weight in the range of 200 to 9000, are suitable for use in the formulation. Additionally, suitable binding agents include, without limitation: starches, gelatins, lactose, mannitol, acacia, cabomer, carboxymethyl celluslose sodium, dextrin, guar gum, hydroxyethyl cellulose, hydroxypropyl cellulose, hydroxypropylmethyl cellulose, lactose, liquid glucose, maltodextrin, methylcellulose, polymethacrylates, having a molecular weight range from about 2,500 to 3,000,000 and their equivalents.

In addition to the afore mentioned ingredients, other ingredients may be added to the mixture before it is ultimately conveyed into the final dosage form. For example, when produced as an oral dosage, such as a chewable table, lozenge, or liquid, flavoring agents, and sweetening agents may be added. Flavoring agents may be chosen based upon the desired flavor. Sweetening agents may also be any type of general sweetening agent such as sugar, saccharin, aspartame, or other natural sweeteners. The dosage is then placed in final form by any additional processing measures required by the specific form, such pressing for tablets, laminating, for transdermal patches, etc.

In one aspect, a composition in accordance with the present invention may consist essentially of the Loquat extract as recited herein. In another aspect, the composition may contain additional ingredients as recited above. In yet another aspect, the composition may be formulated for oral dosage. In a further aspect, the oral dosage form may be a tablet. In an additional aspect, the oral dosage form may be a capsule. In yet an additional aspect, the oral dosage form may be a beverage, or other food item.

The specific dosage amount of Loquat extract required in order to provide a therapeutic effect may vary somewhat from individual to individual depending on a variety of physiologic factors. Those of ordinary skill in the art will understand this, and will further be able to determine proper dosage amounts for specific individuals through routine monitoring and adjustment of the physiological effects of a give dosage. However, as a general matter, the Loquat extract dosage amount administered to a subject may be from about 150 to about 500 mg/kg of body weight. In another aspect, the dosage amount may be about 325 mg/kg of body weight.

With such dosage amounts in mind, the specific dosage forms may be designed to attain a desired concentration of Loquat extract active ingredients. In one aspect, the amount of Loquat extract in the dosage form may be sufficient to provide a corosolic acid dosage of from about 0.1 mg/g to about 5 mg/g of the dosage formulation. In another aspect, the corosolic acid dosage may be about 3 mg/g.

EXAMPLES

Example 1

A Loquat extract was prepared as follows. Approximately 3 kilograms of Loquat leaf pieces were soaked in approximately 3 liters of an 80% aqueous ethanol solution at 90° C. for 2 hours. The resultant extract solution was filtered, and the leaf pieces collected and soaked in another solution of ethanol having the same parameters for an additional 1 hour. After filtering of the second extract solution, both extract solutions were combined and the alcohol was recovered and the extract concentrated under reduced pressure. The concentrated extract was then dried and pulverized to yield approximately 300 grams of powdered extract containing about 7% corosolic acid content.

Example 2

Figure 2:
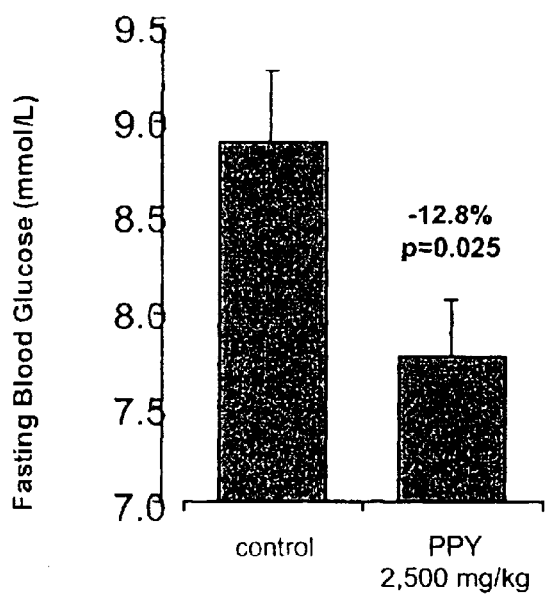
FIG. 2 shows a graphical representation of the fasting blood glucose results obtained in normal subjects by administration of compositions employing a Loquat (Pi Pa Ye "PPY") extract obtained using an extraction process in accordance with one embodiment of the present invention.
Figure 3:
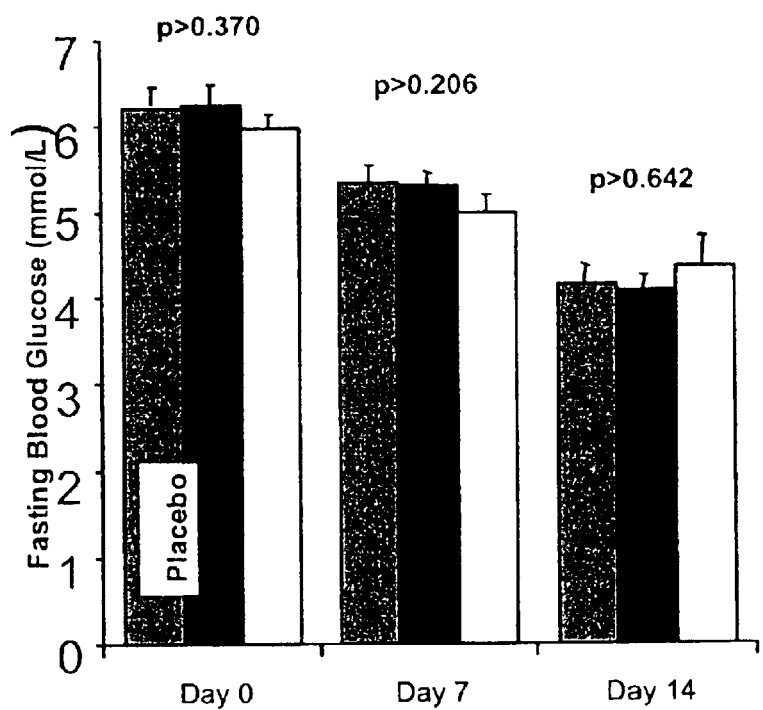
FIG. 3 shows a graphical representation of the fasting blood glucose results for 0, 7, and 14 days, obtained in normal subjects by administration of compositions employing a Loquat (Pi Pa Ye "PPY") extract obtained using an extraction process in accordance with one embodiment of the present invention.
Figure 4:
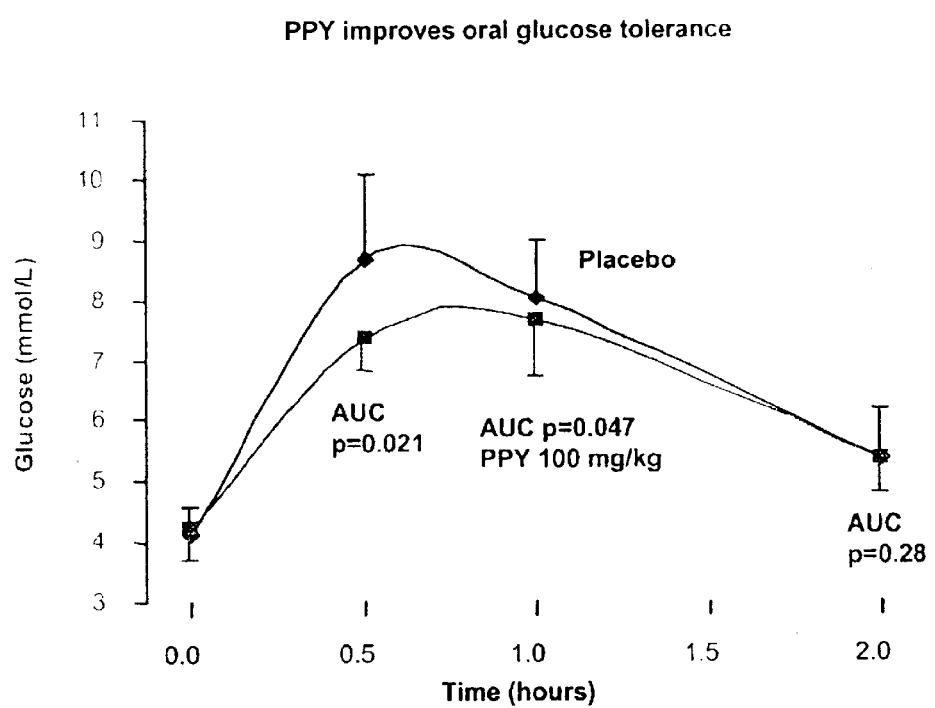
FIG. 4 shows a graphical representation of oral glucose tolerance results upon receipt of a glucose bolus dose, achieved by normal subjects after 5–7 days of administration of compositions employing a Loquat (Pi Pa Ye "PPY") extract obtained using an extraction process in accordance with one embodiment of the present invention.
Figure 5:
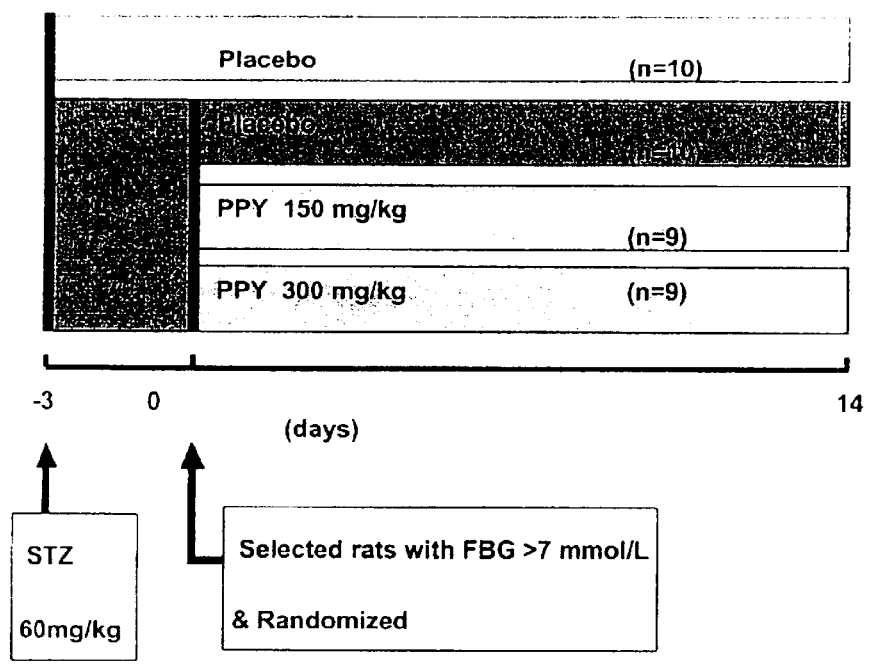
FIG. 5 shows a graphical representation of the STZ-induced diabetic subjects enrolled in a clinical study using compositions employing a Loquat (Pi Pa Ye) extract obtained using an extraction process in accordance with one embodiment of the present invention.
Figure 6:
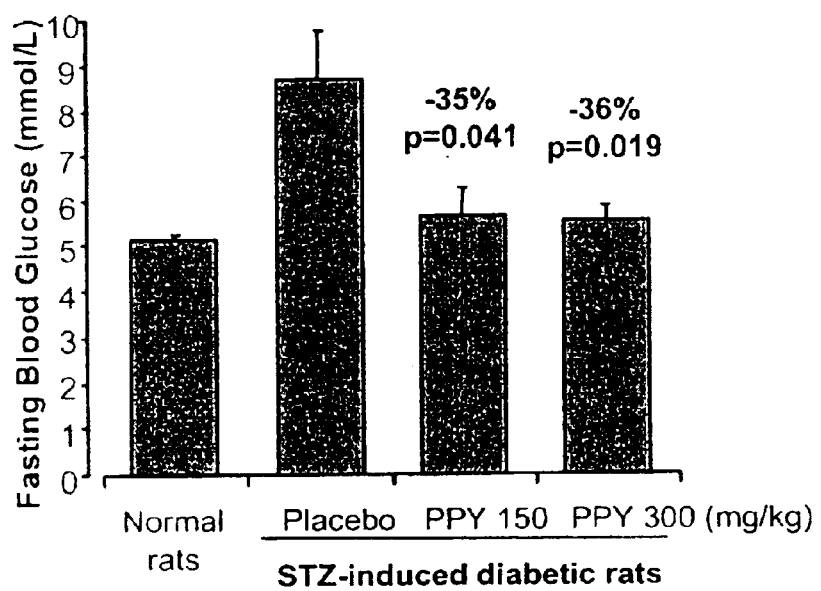
FIG. 6 shows a graphical representation of the fasting blood glucose results obtained in STZ-induced diabetic subjects by administration of compositions employing a Loquat (Pi Pa Ye "PPY") extract obtained using an extraction process in accordance with one embodiment of the present invention.

The Loquat extract of Example 1 was administered to mice or rat test subjects for 5 days at doses of 150 to 500 mg/kg of body weight. As shown in FIGS. 1, 2, and 3, fasting blood glucose levels were significantly decreased as opposed to animals that were administered a placebo. Further, as shown in FIG. 4, after 5 to 7 days of administration, those subjects who received the above-recited formulation had oral glucose tolerance test results that yielded significantly lower blood glucose levels at 0.5 to 2 hours after administration of an oral bolus glucose dose, than those subjects to which placebos were administered. Additionally, FIGS. 5 and 6 show similar blood glucose modulating results in subjects that are STZ-induced diabetic.

Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function, manner of operation, assembly, and use may be made without departing from the principles and concepts set forth herein.

What is claimed is:

1. A method of making a Loquat extract having a standardized corosolic acid concentration of about 7% w/w comprising:
   a) providing a mixture of small pieces of a Loquat source material in an 80% aqueous ethanol solution at about a 1:1 wt./vol. ratio;
   b) soaking the small Loquat leaf pieces in the ethanol solution at a temperature of from about 90° C. for about 2 hours, to create an extract solution;
   c) filtering the extract solution and collecting the filtrate and reclaiming the small Loquat material;
   d) soaking the reclaimed small Loquat material pieces in an aqueous ethanol solution at about a 1:1 wt./vol. ratio and at a temperature of about 90° C. for about 1 hour, to create a second extract solution;
   e) filtering the second extract solution and collecting the filtrate;

f) combining the filtrates into a single filtrate; and g) concentrating the filtrate, thereby providing a Loquat extract containing a standardized corosolic acid concentration of about 7% w/w.

2. The method of claim 1, further comprising the steps of:

h) drying the concentrated filtrate and;

i) pulverizing the filtrate into a powder.

3. The method of claim 1, wherein the Loquat source material comprises Loquat leaves.

4. The method of claim 1, wherein the Loquat source material consists of Loquat leaves.

5. The method of claim 1, wherein the Loquat source material is obtained from plant species *Eriobotrya japonica*.

\* \* \* \* \*